United States Patent
Okuno

(10) Patent No.: US 7,306,708 B2
(45) Date of Patent: Dec. 11, 2007

(54) LIMITING CURRENT TYPE OXYGEN SENSOR

(75) Inventor: Tatsuyuki Okuno, Shizuoka (JP)

(73) Assignee: Yazaki Corporation, Tokyo (JP)

( * ) Notice: Subject to any disclaimer, the term of this patent is extended or adjusted under 35 U.S.C. 154(b) by 778 days.

(21) Appl. No.: 10/649,744

(22) Filed: Aug. 28, 2003

(65) Prior Publication Data
US 2004/0040845 A1 Mar. 4, 2004

(30) Foreign Application Priority Data
Aug. 30, 2002 (JP) .............................. 2002-253339

(51) Int. Cl.
*G01N 27/41* (2006.01)
(52) U.S. Cl. .................. 204/425; 204/429; 73/23.32
(58) Field of Classification Search ................ 204/424, 204/425, 429; 205/783.5; 73/23.32
See application file for complete search history.

(56) References Cited

U.S. PATENT DOCUMENTS

| | | | |
|---|---|---|---|
| 4,668,374 A * | 5/1987 | Bhagat et al. | 204/412 |
| 5,366,611 A * | 11/1994 | Ioannou et al. | 204/412 |
| 5,814,719 A * | 9/1998 | Suzuki et al. | 73/23.31 |
| 6,007,688 A * | 12/1999 | Kojima et al. | 204/426 |

FOREIGN PATENT DOCUMENTS

| | | |
|---|---|---|
| DE | 103 39 944 A1 | 3/2004 |
| JP | 61-97753 | 6/1986 |
| JP | 2507842 | 5/1996 |

OTHER PUBLICATIONS

German Office Action dated May 13, 2005 and English translation (5 pages).

* cited by examiner

*Primary Examiner*—Kaj K. Olsen
(74) *Attorney, Agent, or Firm*—Kratz, Quintos & Hanson, LLP

(57) ABSTRACT

In a limiting current type oxygen sensor, a plane cathode layer and a plane anode layer are arranged on both sides of a solid electrolyte layer, and a porous diffusion layer for controlling gaseous diffusion rate is arranged on the other side of the cathode layer. Additionally, the cathode layer has a bonding pad portion for connecting electrically to an external lead wire. A part of the bonding pad is in contact with the solid electrolyte layer, and the other part of the bonding pad is exposed to an atmosphere of the sensor. A patterned gas barrier film is disposed in between a boundary between the part of the bonding pad being in contact with the patterned solid electrolyte layer and the other part of the bonding pad exposed to the atmosphere, and surroundings thereof so as not to expose the boundary directly to the atmosphere.

1 Claim, 5 Drawing Sheets

LIMITING CURRENT TYPE OXYGEN SENSOR

BACKGROUND OF THE INVENTION

1. Field of the Invention

This invention relates to a limiting current type oxygen sensor, in particular, to a limiting current type oxygen sensor that can correctly measure oxygen concentration in a low concentration range even if applied voltage is unstable.

2. Description of the Related Art

The limiting current type oxygen sensor having a four-layer structure consisting of a porous diffusion layer for controlling gaseous diffusion rate, a cathode layer, a solid electrolyte layer and an anode layer can measure without reference gas and the like, output current linear to the gas concentration, and accurately measure the concentration from a low concentration level to a high concentration level. Therefore, a growing number of conventional concentration cell type sensors with conventional solid electrolyte layer are replaced by the limiting current type oxygen sensors.

FIGS. 1A and 1B show an example of the conventional limiting current type oxygen sensor. FIG. 1A is a top view, and FIG. 1B is a cross-sectional view taken on line L-L of FIG. 1A.

In this limiting current type oxygen sensor, a plane cathode layer 101 and a plane anode layer 103 are arranged on both sides of a solid electrolyte layer 102, and a porous diffusion layer 104 for controlling gaseous diffusion rate is arranged on the other side of the cathode layer 101. Additionally, the cathode layer 101 has a bonding pad 105 for connecting electrically to an external lead wire. A part of the bonding pad 105 is covered with the solid electrolyte layer 102, and the other part of the bonding pad 105 is exposed to an atmosphere.

A principle of the limit current type oxygen sensor will be described below with reference to FIG. 2. By applying voltage between the cathode layer 101 and the anode layer 103 via the solid electrolyte layer 102, firstly oxygen gas at the cathode layer 101 is ionized. Then, the ionized oxygen is shifted to the anode layer 103 through the solid electrolyte layer 102 previously heated to a suitable temperature for ion conduction by a heater (not shown). Then, this ionized oxygen returns to the oxygen gas at an interface between the anode layer 103 and the solid electrolyte layer 102. At this moment, a current corresponding linearly to the shifting ionized oxygen, namely linear to the oxygen gas supplied to the cathode layer 101, flows from the anode layer 103 to the cathode layer 101.

In this case, as indicated by a bold arrow in FIG. 2, the oxygen gas is supplied to the cathode layer 101, through the porous diffusion layer for controlling gaseous diffusion rate 104 (hereafter referred to as a "diffusion layer") from the atmosphere. The supply is regulated by the diffusion layer 104 structured optimally, and proportional to the oxygen gas concentration in the atmosphere. Therefore, the oxygen concentration in the atmosphere is known by only measuring the current from the anode layer 103 to the cathode layer 101 as the limiting current.

In a sensor having a common form as shown in FIG. 2, FIG. 3 shows a relation diagram between voltage, applied the cathode layer 101 and the anode layer 103, and current (sensor output) at 20.6% of oxygen concentration in the atmosphere surrounding the sensor.

In FIG. 3, a region indicated by "a" is a resistance region, a region indicated by "b" is a limiting current region, and a region indicated by "c" is a overcurrent region. In the limiting current region as the region b, the sensor output (current) is regarded as independent of the applied voltage, and a relation between the oxygen concentration and the sensor output (current) is regarded as linear.

However, as shown by a broken-line arrow in FIG. 2, the oxygen gas supplied to the cathode layer 101 through the porous diffusion layer 104 is supplied through not only a backside of the porous diffusion layer 104 corresponding to the cathode layer 101 originally expected, but also a side surface of the porous diffusion layer 104 or a surface exposed at the cathode layer 101 side. Therefore, a characteristic curve of the relation at the region b in FIG. 3 has a positive slope and linearity of the relation between the oxygen concentration and the output is degraded. In this case, measurement accuracy is influenced greatly by voltage drift. Otherwise, a linearity compensation circuit is needed to maintain the measurement accuracy. Resultingly this increases cost and power consumption of the sensor, and creates other problems.

To solve these problems, a method of preventing inflow of the oxygen from an unnecessary part by covering parts other than an originally expected passage of oxygen with a gas barrier layer such as glass or gas barrier alumina is proposed by Japanese Utility Model Application Laid-Open No. Show 61-97753, Japanese Utility Model Application Laid-open No. Hei 3-104849 and the like.

However, according to these, heat capacity and power consumption of the sensor is increased. Therefore, a load of the heater for heating the sensor to its operating temperature, namely a temperature suitable for oxygen ion conduction in the solid electrolyte layer, is increased and a lifetime of the heater is decreased. Additionally, required time from power-on to the sensor operating temperature being stabilized by heating is increased. Therefore, there are problems such as time-consuming measurement or considerable power consumption in an intermittent measurement for use in low power for such as battery powered applications. Further, there are problems such as a short lifetime or a lack of reliability of the gas barrier layer because of peeling or cracking of the gas barrier layer caused by a difference among coefficients of thermal expansion and a temperature difference at the intermittent measurement.

Moreover, according to the invention as described in Japanese Utility Model Application Laid-open No. Hei 3-104849, there is provided a limiting current type oxygen sensor which can measure oxygen gas precisely from low to high concentration of the oxygen gas. However, since alumina as a gas barrier layer is needed to deposit on either side surface of the sensor, film deposition process becomes complicated, and as a result, cost of the sensor may be increased.

SUMMARY OF THE INVENTION

Accordingly, it is an object of this invention to provide a low-cost current limiting type oxygen sensor having a flat characteristic curve slanting upward very little in the current limiting region at low oxygen concentration, said sensor being able to measure reliably and correctly, said sensor not necessarily requiring an expensive complicated compensation circuit consuming considerable power.

After examining the limiting current type oxygen sensor in detail, it turned out that oxygen gas is supplied directly from an atmosphere of the sensor, namely without a diffusion control by the porous diffusion layer 104, through a boundary between a part covered with the solid electrolyte layer 102 and a part exposed to the atmosphere of the bonding pad 105 as indicated by a broken-line arrow in FIG. 5, then the oxygen gas is ionized to produce oxygen ions, which serve as a noise according to applied voltage, to reduce the measurement accuracy remarkably in a low concentration region as shown in FIG. 4. Further, it turned out that when taking measures against just said boundary, an obtained effect is sufficient enough for applications in the low concentration region, such as an atmosphere controlled furnace of a glove box, a nitrogen reflow furnace or the like without a gas barrier layer covering over the whole surface of the sensor, and resulted in the present invention.

The object of the invention has been achieved by providing a limiting current type oxygen sensor comprising a patterned cathode layer, a patterned anode layer, a patterned solid electrolyte layer disposed in between one surface of the cathode layer and the anode layer, a patterned gas barrier film, and a plane porous diffusion layer for controlling gaseous diffusion rate disposed on the other surface of the cathode layer, wherein said cathode layer has a bonding pad portion for connecting electrically with an external lead wire, a part of the bonding pad is covered with the patterned solid electrolyte layer, and the other part of the bonding pad is exposed to an atmosphere of the sensor, wherein said patterned gas barrier film is disposed in between the bonding pad and the patterned solid electrolyte layer at a boundary between the part of the bonding pad being in contact with the patterned solid electrolyte layer and the other part of the bonding pad exposed to the atmosphere, and surroundings thereof.

The object of the invention has been also achieved by providing a limiting current type oxygen sensor comprising a patterned cathode layer, a patterned anode layer, a patterned solid electrolyte layer disposed in between one surface of the cathode layer and the anode layer, a patterned gas barrier film, and a plane porous diffusion layer for controlling gaseous diffusion rate disposed on the other surface of the cathode layer, wherein said cathode layer has a bonding pad portion for connecting electrically with an external lead wire, a part of the bonding pad is covered with the patterned solid electrolyte layer, and the other part of the bonding pad is exposed to an atmosphere of the sensor, wherein a boundary between the part of the bonding pad being in contact with the patterned solid electrolyte layer and the other part of the bonding pad exposed to the atmosphere, and surroundings thereof are covered with said patterned gas barrier film.

According to any one of these structures, it is possible to acquire a limiting current type oxygen sensor with high accuracy having a flat characteristic curve in a current limiting region in the low oxygen concentration region with a troublesome gas barrier film covering only a small area of the sensor.

The limiting current type sensor of this invention can always measure correctly in the low oxygen concentration region even if applied voltage drifts a little. Moreover, since linearity between detected concentration and signal output is very good in the low oxygen concentration region, said sensor not only can measure very precisely but also requires no expensive compensation circuit consuming considerable power, so that a measuring apparatus having the limiting current type oxygen sensor can be made at low cost and operated for a longer time on battery.

According to this invention as described above, since a tiny area of the gas barrier film is sufficient, problems arising among conventional sensors having a large area of the gas barrier film such as an increase in heat capacity or thermal history may not arise in the sensor of this invention.

Such a gas barrier film can be made of alumina, glass and the like, and can be obtained by PVD, CVD, sputtering or coating. In this case, it is necessary to examine such as a thickness and a size of the gas barrier film previously so as to obtain a sufficient effect. In addition, as a gas barrier film, alumina is preferable because of the sensor being operated at high temperature, difference of thermal expansion coefficients among the gas barrier film, the solid electrolyte layer and the porous diffusion layer, cost, handling and the like.

In the limiting current type oxygen sensor of this invention, porous material having activity to change oxygen gas in the atmosphere into oxygen ion such as platinum, gold or nickel, and porous material having activity to return the oxygen ion to the oxygen gas are used for the cathode layer and the anode layer respectively.

It is necessary to use such as fully stabilized zirconia or bismuth oxide, through which the oxygen ion can pass, as the solid electrolyte layer.

It is necessary to use material having suitable diffusion controllability and sufficient heat resistance such as porous alumina as the gas barrier film.

It is not necessary that the heater is made of porous material. Usually, the heater is formed in a zigzag line shape. Since sufficient durability is required of the heater, platinum or the like is used for the heater material.

DESCRIPTION OF THE PREFERRED EMBODIMENT

Figure 1A:
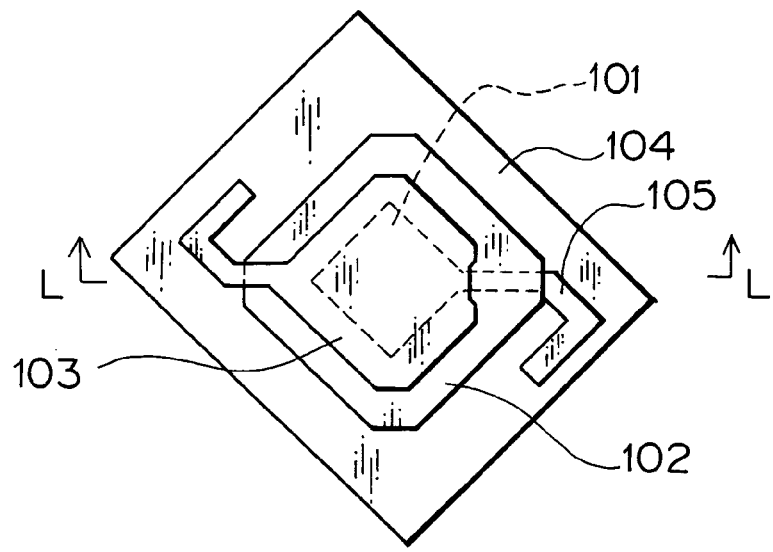
FIG. 1A is a top view showing conventional limiting current type oxygen sensor.
Figure 1B:
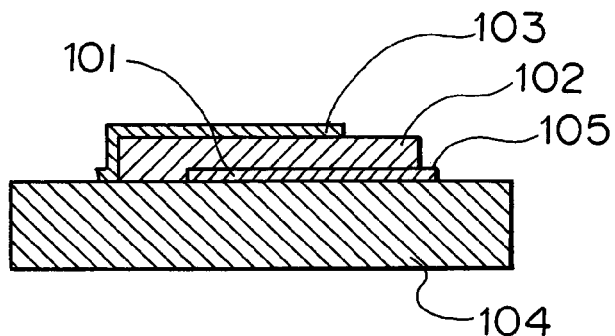
FIG. 1B is a section view taken on line L-L of FIG. 1A.
Figure 2:
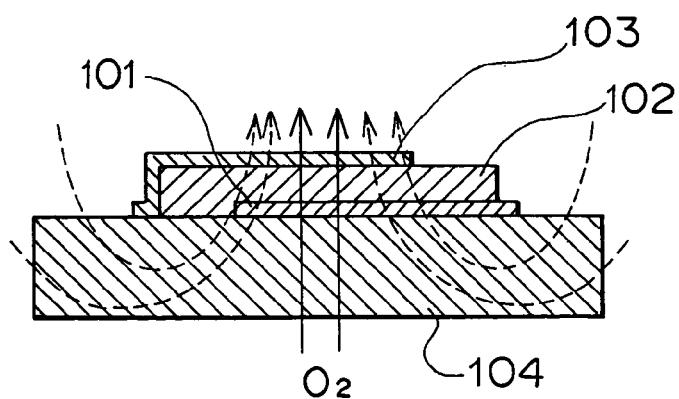
FIG. 2 is a section view explaining the principle of the limiting current type oxygen sensor.
Figure 3:
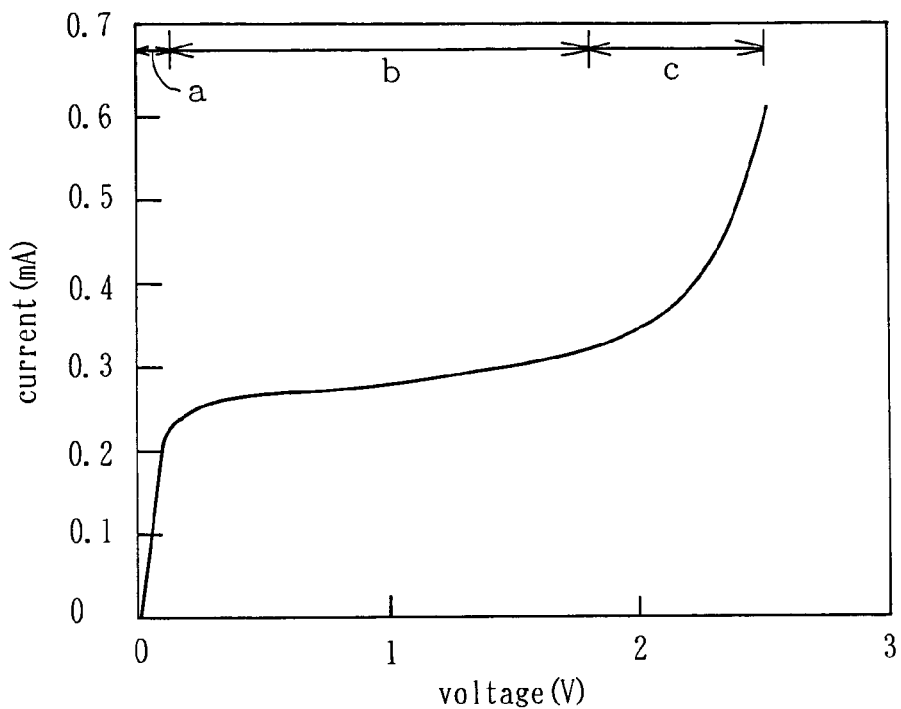
FIG. 3 is an example of a current-voltage diagram of the limiting current type oxygen sensor.
Figure 4:
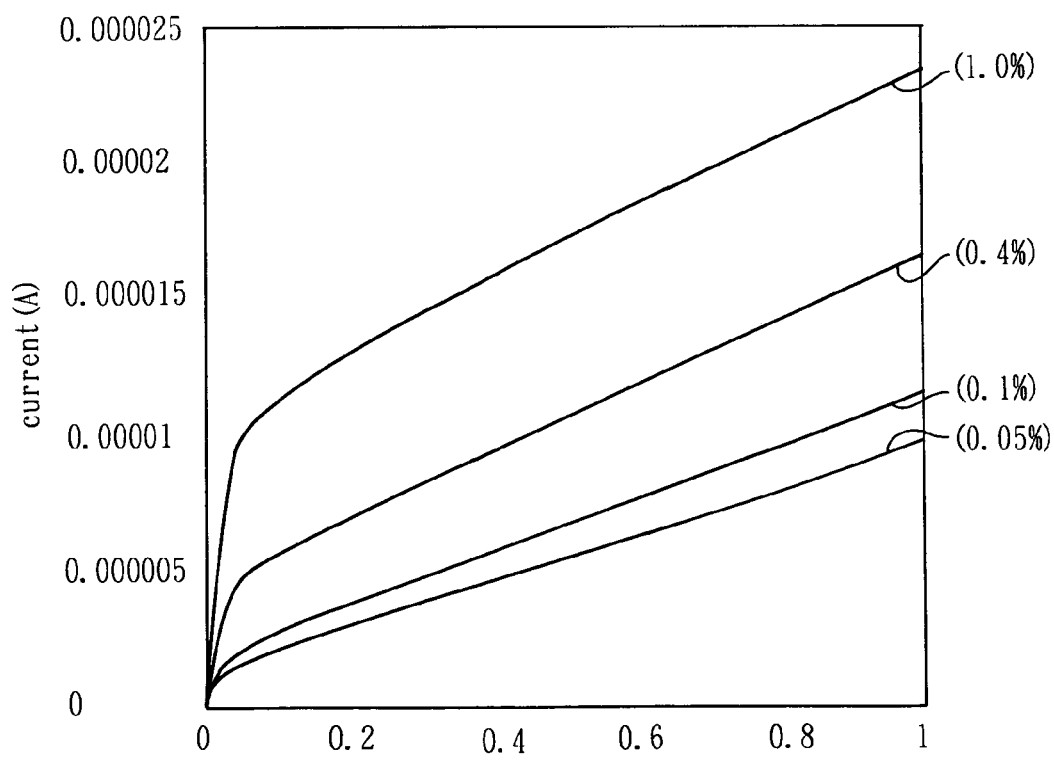
FIG. 4 is a diagram showing a relation between applied voltage and output current of the conventional limiting current type oxygen sensor at several oxygen concentration conditions including a low oxygen concentration.
Figure 5:
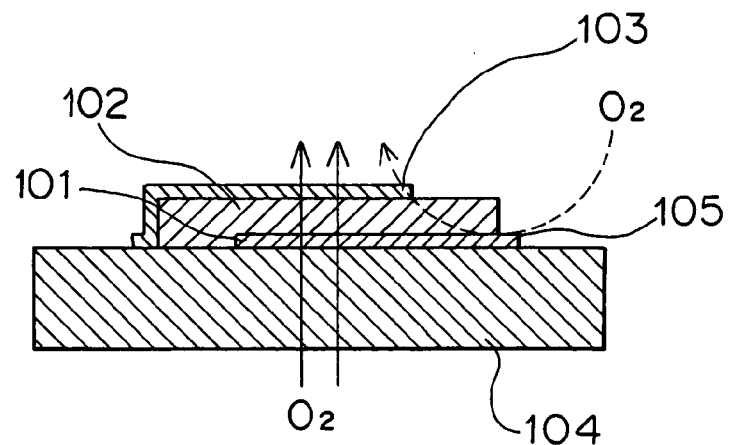
FIG. 5 is a view for explaining why the conventional limiting current type oxygen sensor has poor accuracy at the low oxygen concentration condition.

A first embodiment of the present invention will now be described below with reference to figurers.

[Preparing Sensors of the First Embodiment and of Reference for Comparison]

First, a porous alumina substrate 104 is employed as a porous diffusion layer 104. As a preprocessing of the substrate 104, after ultrasonic cleaning in acetone, the substrate 104 is heated up to about 1000 degrees Celsius.

Next, a heater in a zigzag line shape (not shown) is formed on one side surface of this substrate 104 by a FR sputtering apparatus. At this time, a part of the surface unnecessary for forming the heater is covered with a metal mask during sputtering. Thereafter, for stabilizing the heater, the heater is baked at 1000 degree Celsius for sixty minutes in air.

Next, a platinum electrode (cathode layer) 101 and its bonding pad 105 are formed by sputtering on a necessary part of the other side surface of the substrate 104 with another metal mask. Then, during masking the surface except a boundary between a part contacting with the solid electrolyte layer 102 and a part exposed to the atmosphere of the bonding pad 105 and its surroundings, a patterned gas barrier film 106 is formed by sputtering a sintering alumina target.

Next, for covering a main part of the cathode layer 101 and a part of the patterned gas barrier film 106 made of coated alumina, a stabilized zirconia layer as a solid electrolyte layer 102 is formed by the RF sputtering apparatus. Then, for oxidizing the stabilized zirconia, the substrate is heated at 700 degree Celsius for 60 minutes in air. Next, a top surface of the processed stabilized zirconia is masked with a metal mask, of which a large hole pattern for forming a main part of the anode layer 103 is so positioned as to overlay said large hole pattern on the main part of the cathode layer 101. Then, a platinum electrode (anode layer) 103 with a bonding pad is formed by sputtering.

Figure 6A:
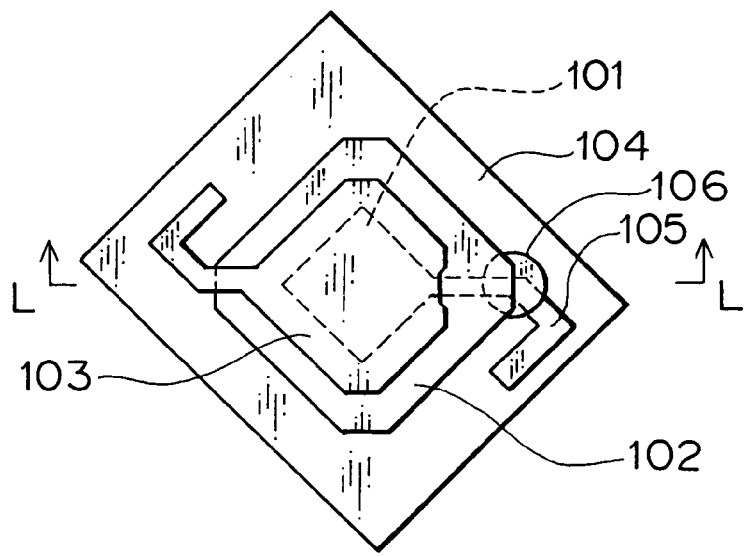
FIG. 6A is a top view showing a first embodiment of a limiting current type oxygen sensor according to this invention.
Figure 6B:
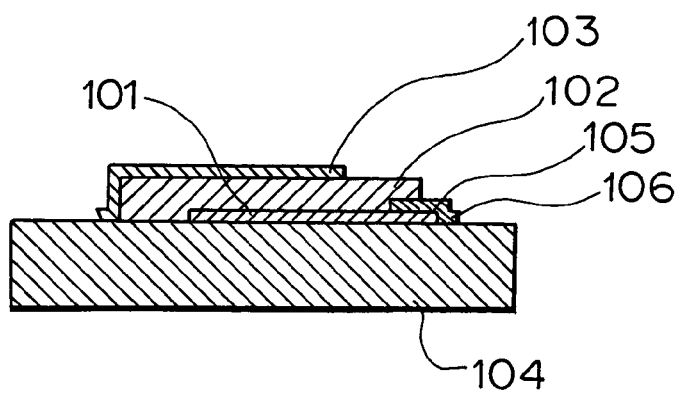
FIG. 6B is a section view taken on line L-L of FIG. 6A.

Thereafter, as the voltage applied to the heater is increased, sweep voltage from 0 to 2 volt is applied between cathode layer and anode layer to transform these electrodes to porous electrodes. Thus, as shown in FIGS. 6A and 6B, the limiting current type oxygen sensor of the first embodiment is prepared.

In addition, a conventional limiting current type oxygen sensor similar to the limiting current type oxygen sensor of the first embodiment except not having the alumina layer as the patterned gas barrier film 106 is prepared as a reference for comparison.

[Evaluation of the Sensors of the First Embodiment and the Reference for Comparison]

Both the sensors of the first embodiment and the reference are heated at 700 degree Celsius by their respective heaters. Then, relations between the applied voltage and output current are measured in nitrogen gases containing oxygen adjusted to 1.0, 0.4, 0.1 and 0.05 volume percent respectively. Measuring results are shown in FIG.7, wherein "embodiment" and "reference" indicate the respective results of the sensor of the first embodiment and the sensor of the reference, and each numeral inside a parenthesis indicates each oxygen concentration (volume percent) in nitrogen gas.

Figure 7:
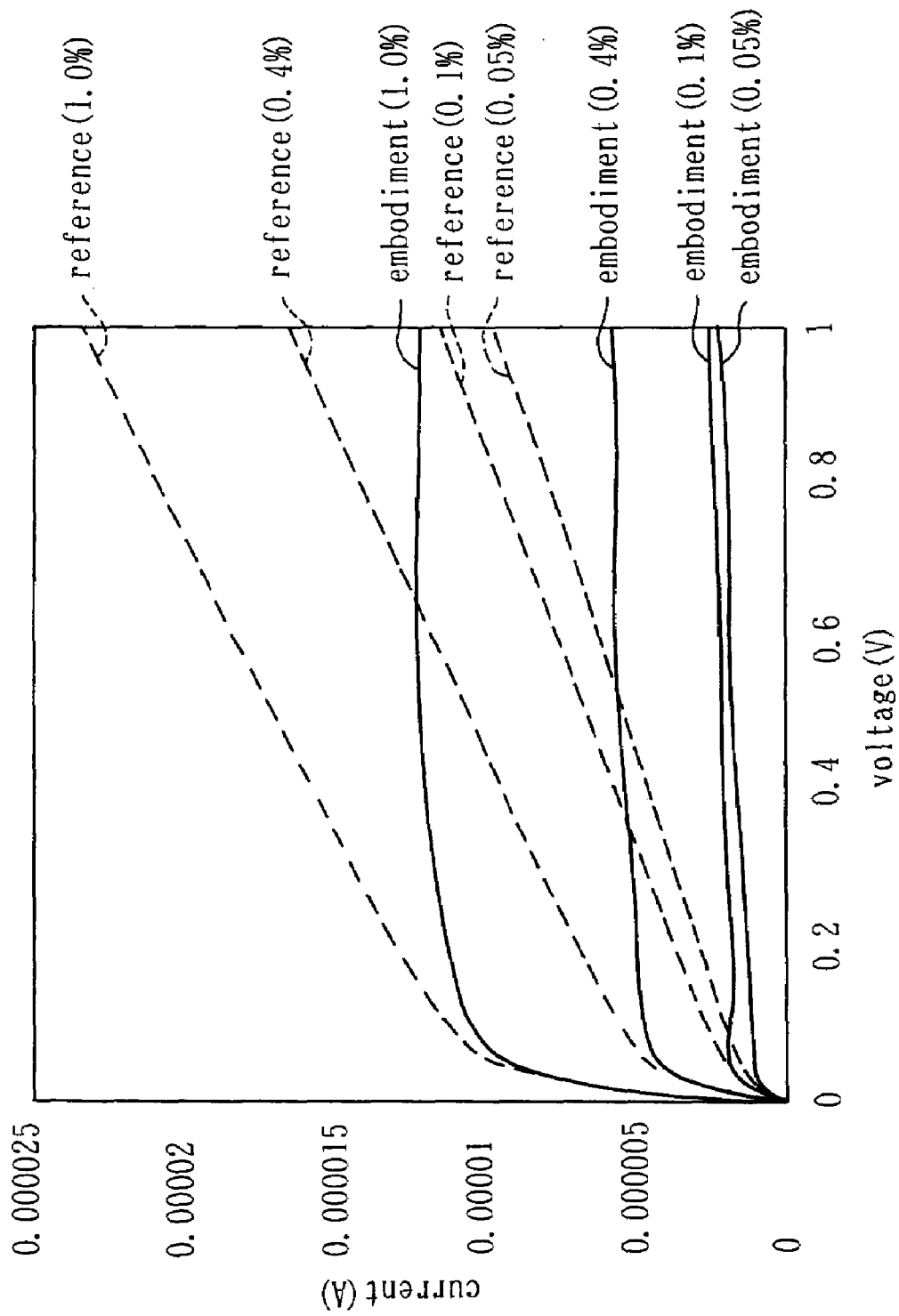
FIG. 7 is a diagram showing relations between applied voltage and output current of both the limiting current type oxygen sensor according to the first embodiment of this invention (continuous line) and the conventional limiting current type oxygen sensor (dashed line) at several oxygen concentration conditions including a low oxygen concentration.

FIG. 7 shows that while output current of the sensor of the reference is largely affected by applied voltage at the limiting current region, output current of the sensor of the first embodiment is hardly affected by applied voltage at the limiting current region, namely, the sensor of the first embodiment can measure correctly even if the applied voltage drifts a little.

Figure 8:
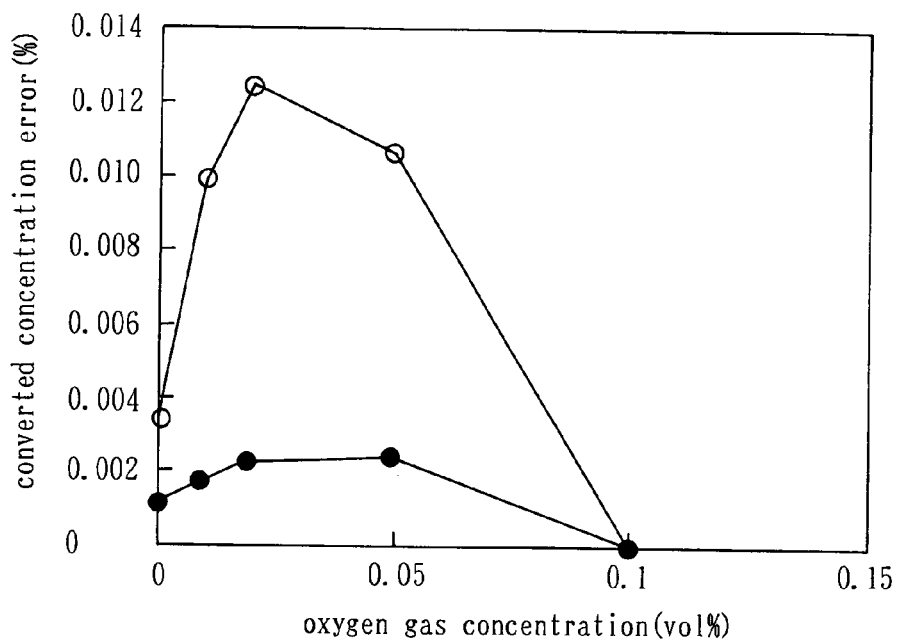
FIG. 8 is a diagram showing relations as a test result between oxygen gas concentration and converted concentration error of both the limiting current type oxygen sensor according to the first embodiment of this invention (black circle) and the conventional limiting current type oxygen sensor (white circle) at an applied voltage of 0.5 volt.

Further, a linearity of the output current of each sensor is evaluated. FIG. 8 shows converted concentration errors calculated from above measurement results, each of converted concentration errors being defined as a difference between real oxygen concentration and converted concentration, said converted concentration being obtained by converting proportionally each output in each oxygen concentration against 1000 parts per million (hereafter abbreviated as "ppm") output, wherein said 1000 ppm output means an output in 1000 ppm oxygen concentration. In FIG. 8, black circles and continuous line indicate measuring result of the sensor of the first embodiment, while white circles and dashed line indicate measurement result of the sensor of the reference.

FIG. 8 shows that the converted concentration error of the sensor of the first embodiment according to this invention is extremely smaller than that of the reference. Therefore, even without any expensive compensation circuit consuming considerable power, the sensor of the first embodiment has linearity being sufficient for satisfying measurement accuracy, for example, plus or minus 3 percent accuracy of 1000 ppm full scale range as a requirement for applying to an industrial controlled atmosphere furnace.

In addition, even when a microprocessing circuit is employed for improving the measurement accuracy further, a simple circuit is sufficient because of few deviations, so that a low-cost low-power-consumption sensor can be employed.

[Preparing and Evaluating a Sensor of a Second Embodiment]

Figure 9A:
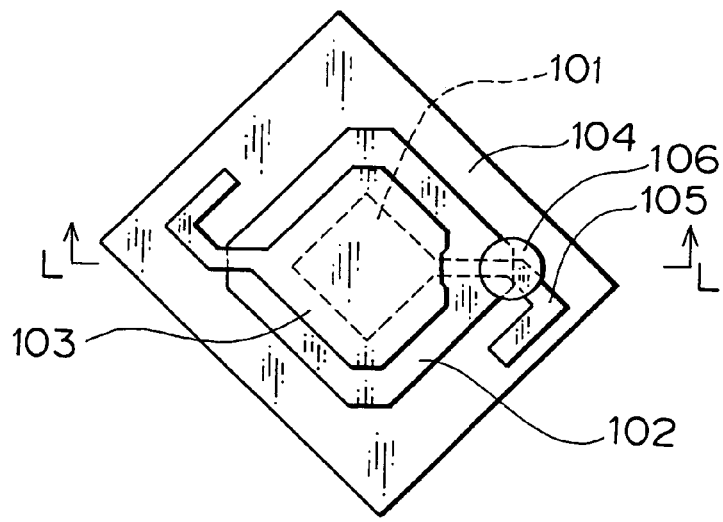
FIG. 9A is a top view showing a second embodiment of the limiting current type oxygen sensor of this invention.
Figure 9B:
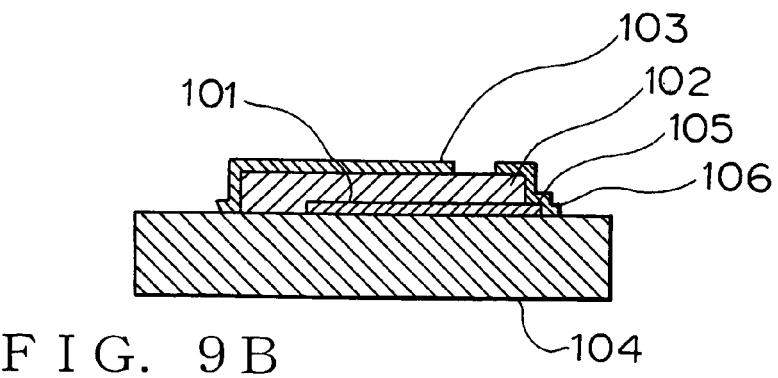
FIG. 9B is a section view taken on line L-L of FIG. 9A.

While the sensor of the first embodiment is the limiting current type oxygen sensor, wherein said patterned gas barrier film is disposed in between the bonding pad and the patterned solid electrolyte layer at a boundary between the part of the bonding pad being in contact with the patterned solid electrolyte layer and the other part of the bonding pad exposed to the atmosphere, and surroundings thereof, the sensor of the second embodiment is a limiting current sensor, wherein a boundary between the part of the bonding pad being in contact with the patterned solid electrolyte layer and the other part of the bonding pad exposed to the atmosphere, and surroundings thereof are covered with said patterned gas barrier film. FIG. 9A shows a top view of the sensor of the second embodiment, and FIG. 9B shows a section view taken on line L-L of FIG. 9A.

The limiting current type oxygen sensor of the second embodiment according to this invention is prepared by followings. Firstly the cathode layer 101 and the bonding pad 105 are formed simultaneously. Secondly the solid electrolyte layer 102 is formed. Thirdly, the anode layer 103 is formed. Fourthly, a boundary between a part covered with the solid electrolyte layer 102 and a part exposed to the atmosphere of the bonding pad 105 and its surroundings are coated with a coating agent of alumina system having high sealing performance. Fifthly, said coated agent is sintered at 150 degree Celsius to be formed as a 500 micrometer thickness patterned gas barrier film 106. Lastly, both the cathode layer 101 and the anode layer 103 are transformed to porous electrodes to be prepared as the second embodiment of the limiting current type oxygen sensor according to this invention.

Converted concentration error of the sensor of the second embodiment prepared in this way is evaluated to ascertain its excellent linearity like the sensor of the first embodiment.

In addition, since the boundary between the bonding pad 105 and the solid electrolyte layer 102 of the sensor of the first embodiment has no exposed area to the atmosphere, such effect of the sensor of the first embodiment is more reliably attained than that of the second embodiment. However, a manufacturing process for the conventional sensor can be easily applied to the sensor of the second embodiment as it is.

Although this invention has been fully described by way of examples with reference to the accompanying drawings, it is to be noted that various changes and modifications can be made in a scope of this invention.

What is claimed is:

1. A limiting current type oxygen sensor comprising:
   a patterned cathode layer;
   a patterned anode layer;
   a patterned solid electrolyte layer disposed in between one surface of the cathode layer and the anode layer;
   a patterned gas barrier film; and
   a plane porous diffusion layer for controlling gaseous diffusion rate disposed on the other surface of the cathode layer,
   wherein said cathode layer has a bonding pad portion for connecting electrically with an external lead wire, a part of the bonding pad is covered with the patterned solid electrolyte layer, and the other part of the bonding pad is exposed to an atmosphere of the sensor,
   wherein said patterned gas barrier film is disposed in between the bonding pad and the patterned solid electrolyte layer at a boundary between the part of the bonding pad being in contact with the patterned solid electrolyte layer and the other part of the bonding pad exposed to the atmosphere, and surroundings thereof.

* * * * *